United States Patent [19]

Okamoto et al.

[11] Patent Number: 5,128,069

[45] Date of Patent: Jul. 7, 1992

[54] LUCIFERIN DERIVATIVES

[75] Inventors: Kaoru Okamoto, Katoh; Toshio Goto, Nakagawa, both of Japan

[73] Assignee: Nippon Zoki Pharmaceutical Co., Ltd., Osaka, Japan

[21] Appl. No.: 496,998

[22] Filed: Mar. 21, 1990

[30] Foreign Application Priority Data

Mar. 22, 1989 [JP]  Japan .................. 1-71037
Apr. 10, 1989 [JP]  Japan .................. 1-91578

[51] Int. Cl.$^5$ .............. C09K 3/00; C07D 471/00; C12Q 1/66; G01N 21/76
[52] U.S. Cl. ................... 252/700; 544/350; 435/8; 436/172; 549/223
[58] Field of Search ............. 252/700; 435/8; 546/118; 549/223; 436/172; 544/350

[56] References Cited

U.S. PATENT DOCUMENTS

| | | | |
|---|---|---|---|
| 4,220,450 | 9/1980 | Maggio | 23/230 |
| 4,246,340 | 1/1981 | Lundin et al. | 435/8 |
| 4,278,761 | 7/1981 | Hastings et al. | 435/8 |
| 4,357,420 | 11/1982 | Bostick et al. | 435/8 |
| 4,492,751 | 1/1985 | Boguslaski et al. | 435/7 |
| 4,614,712 | 9/1986 | Baldwin et al. | 435/4 |
| 4,665,022 | 5/1987 | Schaeffer et al. | 435/7 |

*Primary Examiner*—Robert L. Stoll
*Assistant Examiner*—C. Harris
*Attorney, Agent, or Firm*—Armstrong, Nikaido, Marmelstein, Kubovcik & Murray

[57] ABSTRACT

The present invention relates to novel luciferin derivatives and salts thereof represented by the following formula (I), which are useful as chemiluminescence reagents.

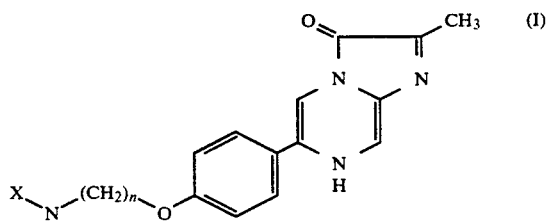

wherein X is hydrogen, an amino-protecting group, R—, R—CO—, R—SO$_2$—, R—NHCO— or R—NH-CS—, R is a fluorescence probe, and n represents an integer of 1 to 4.

4 Claims, 1 Drawing Sheet

LUCIFERIN DERIVATIVES

BACKGROUND OF THE INVENTION

The present invention relates to novel luciferin derivatives and salts thereof, which are useful as chemiluminescence reagents.

In recent years, chemiluminescence microanalyses of the substances in a living body have been often used, and many chemiluminescence substances such as luminol derivatives and oxalic esters have been developed and are employed. After a chemiluminescence compound was found in luciferins which were known as bioluminescence substances, various kinds of chemiluminescence compounds specific for detecting active oxygen and the like were synthesized. However, in case of detecting active oxygen in the presence of living body's components, interference by the contaminating substances having absorption or fluorescence in the visible region often makes the detection difficult. Thus, we are desiring new chemiluminescence substances emitting longer wavelengths luminescence.

An object of the present invention is to provide novel luciferin derivatives and salts thereof, which are useful as chemiluminescence reagents.

RELIEF DESCRIPTION OF THE DRAWINGS

FIG. 1 shows emission spectrum of Compound 1 of the present invention in chemiluminescence system.

DETAILED DESCRIPTION OF THE INVENTION

Figure 1:
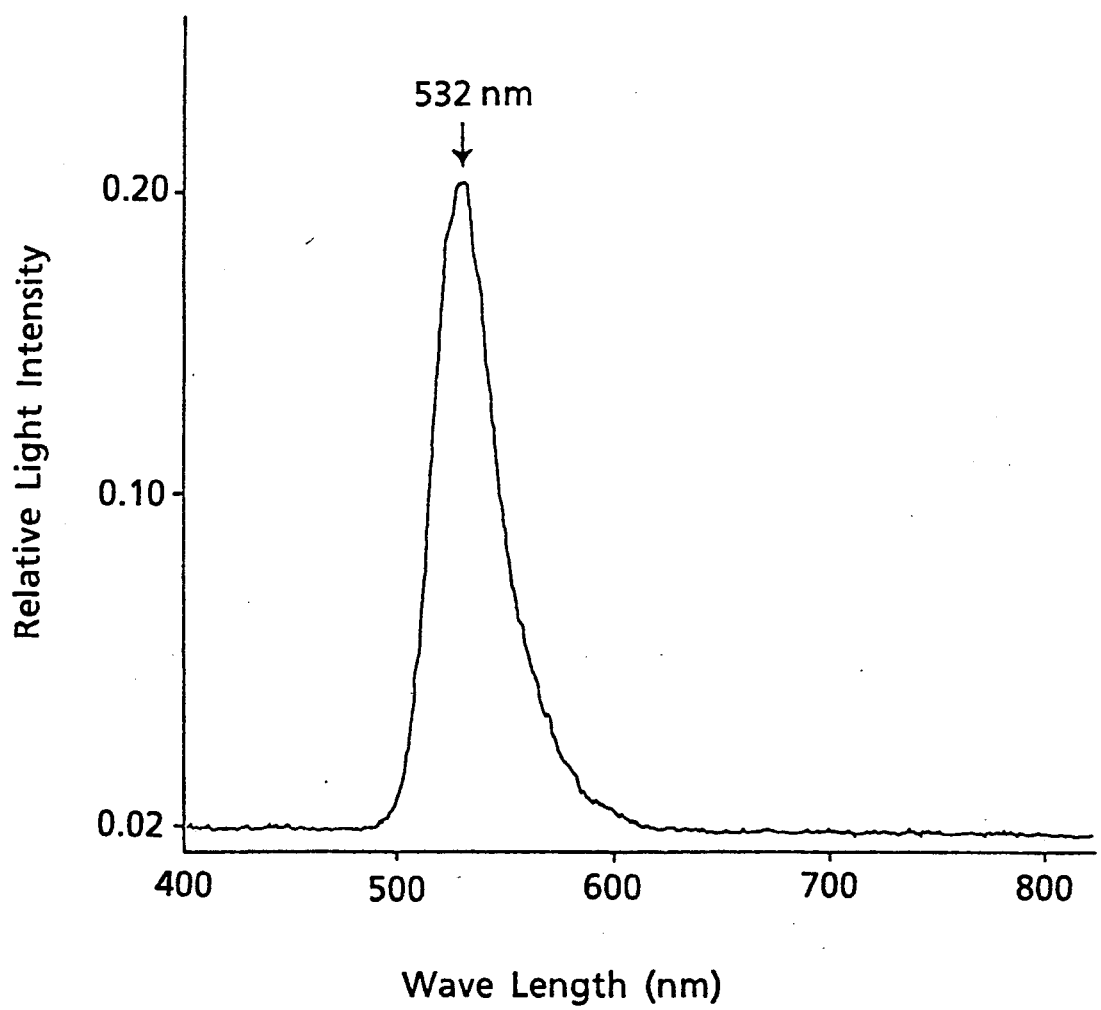

The novel luciferin derivatives of the present invention are represented by the following formula (I):

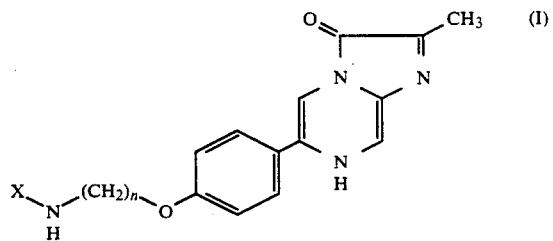

wherein X is hydrogen, an amino-protecting group, R—, R—CO—, R—SO₂—, R—NHCO— or R—NHCS—, R is a fluorescence probe, and n represents an integer of 1 to 4.

In the formula (I), X represents hydrogen, R—, R—CO—, R—SO₂—, R—NHCO—, R—NHCS—, or an amino-protecting group, which may be used include protecting groups for the amino group conventionally employed in peptide synthesis chemistry, for example, benzyloxycarbonyl, p-methoxybenzyloxycarbonyl, p-chlorobenzyloxycarbonyl, p-nitrobenzyloxycarbonyl, p-phenylazobenzyloxycarbonyl, p-methoxyphenylazobenzyloxycarbonyl, t-butoxycarbonyl, t-amyloxycarbonyl, p-biphenylisopropyloxycarbonyl, diisopropylmethyloxycarbonyl, formyl and the like.

As the fluorescence probe of R in the formula (I), a fluorescence probe having the excited wavelengths range substantially overlapping with the range of the emission wavelengths of 3,7-dihydro-6-(4-methoxyphenyl)-2-methylimidazo[1,2-a]pyradin-3-one, preferably the range of the excited wavelengths in from 400 nm to 530 nm, more preferably from 470 nm to 510 nm, for example, fluorescein, 4-dimethylaminophenylazobenzene, 4-nitrobenz-2-oxa-1,3-diazole and the like can be employed.

The luciferin derivatives of the present invention include salts of the compounds having formula (I) above, for example, salts with alkali metal such as sodium, potassium or lithium, salts with alkaline-earth metal such as magnesium, calcium or barium, salts with other metals such as aluminum, or salts as acid addition with an acid such as hydrochloric acid, sulfuric acid, nitric acid, phosphoric acid, formic acid, acetic acid, citric acid, lactic acid, hydrobromic acid or trifluoroacetic acid, or salts with bases such as ammonia or organic amines.

These salts can be produced from free luciferin derivatives in the usual way or can be interchanged with each other.

The luciferin derivatives of the present invention may be prepared as follows.

The compounds represented by the formula (II):

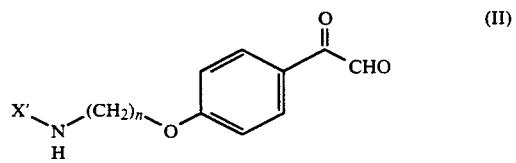

wherein X' is an amino-protecting group, and n represents an integer of 1 to 4, are condensed with 2-aminoacetamidine in an aqueous solution of potassium hydroxide to convert the said glyoxal compounds into pyradine derivatives. The resulting products are reacted in methanol with an aqueous solution of methylglyoxal to give 3,7-dihydro[1,2-a]pyradin-3-one derivatives corresponding to the present compounds of the formula (I) wherein X is an amino-protecting group.

The amino-protecting group is removed from the 3,7-dihydro[1,2-a]pyradin-3-one derivatives to give the compounds of the present invention of the formula (I) wherein X is hydrogen. For example, in the case that benzyloxycarbonyl is used as the amino-protecting group, the protecting group can be removed by a conventional method such as a catalytic reduction, or a treatment with hydrogen bromide-acetic acid.

Various kinds of substituents can be introduced into the amino position of the said compounds from which the protecting group is removed. Therefore, the compounds are very useful as starting materials when a fluorescence probe would be introduced into a luciferin structure.

Subsequently, a fluorescence probe having a functional group which can combine with amines is condensed with the compounds of the present invention of the formula (I) wherein X is hydrogen to give the chemiluminescence substances of the present invention of the formula (I) wherein X is R—, R—CO—, R—SO₂—, R—NHCO— or R—NHCS— (R represents a fluorescence probe). As the condensation method with amines, a replacement reaction of an elimination group such as halogen, a condensation reaction between acid halide and active ester conventionally employed in peptide synthesis, a reaction with isocyanate or isothicyanate and the like can be employed. The condensation reactions can be carried out according to the reaction conditions conventionally employed in the field of peptide synthesis and fluorescence labeling of amines. The fluorescence probes having functional groups which can combine with amines, for example, 5- or 6-carboxyfluorescein succinimidyl ester, 5- or 6-carboxyfluoresceinamidocaproic acid N-hydroxysuccinimide ester, fluorescein-5-isocyanate, fluorescein-5-isothiocyanate, 5-(4,6-ichlorotriazin-2-yl)-aminofluorescein dihydrochloride, 4-dimethylaminoazobenzene-4'-sulfonyl chloride, 4-dimethylaminoazobenzene-4'-isothiocyanate, 4-chloro-7-nitrobenz-2-oxa-1,3-diazole, 4-fluoro-7-nitrobenz-2-oxa-1,3-diazole and the like can be employed.

The resulting compounds of the present invention can be purified by known methods such as distillation chromatography and recrystallization. Identification is established through, inter alia, melting point, elemental analysis, IR, NMR, UV, mass spectrum, etc.

EXAMPLES

The following examples, which are illustrative only and not intended to limit the scope of the invention, describe the preparation of the compounds of the present invention.

EXAMPLE 1

(1) To ice-cold solution of 2-aminoethanl (2.1 mol) in 50% ethanol (800 ml), 100 ml of benzyl chloroformate was slowly added. After stirring for 2 hrs at the same temperature, the mixture was concentrated to the half volume. The residue was acidified (pH 2) with 1N sulfuric acid and extracted three times with chloroform. The extracts were washed with water, dried over anhydrous sodium sulfate, and evaporated to give an oil, which was crystallized from ethanol to give 115 g of 2-(N-benzyloxycarbonylamino)-ethanol as white needles.

m.p.: 55°–57° C.

IR (KBr): 3330, 1692, 1540, 1275, 1210, 1143, 1032, 993, 742, 695 cm$^{-1}$.

MS (EI, 20eV): m/z 195 (M+),

NMR(CDCl$_3$): δ=2.87(1H,br.s), 3.25–3.35(2H,m), 3.66(2H,t,J=4.6Hz), 5.08(2H,s), 5.42(1H,br), 7.25–7.40(5H,m).

(2) To a solution of the resulting product (28 g) in pyridine (200 ml), 25 g of p-toluenesulfonyl chloride was added. The mixture was stirred at 0° C. for 1 hr, poured into ice-water, acidified with 6N HCl, and extracted with ethyl acetate. The extracts were washed with water and brine, dried over anhydrous sodium sulfate, and evaporated to give 43 g of 2-(N-benzyloxycarbonylamino)ethyl p-toluensulfonate as an oil.

IR (Neat): 3350, 1730, 1498, 1455, 1215, 1160, 1121, 1080, 1035, 1021, 816, 738, 685 cm$^{-1}$.

NMR(CDCl$_3$): δ=2.43(3H,s), 3.44(2H,dt,J=5.0, 5.3Hz), 408(2H,t,J=5,0Hz), 5.05(2H,s), 5.17(1H,br.t), 7.25–7.45(5H,m), 7.32(2H,d,J=9.0Hz), 7.77(2H,d,J=9.0Hz).

(3) A mixture of 35 g of 2-(N-benzyloxycarbonylamino)ethyl p-toluenesulfonate, 13 g of 4'-hydroxyacetophenone and 55 g of anhydrous potassium carbonate in 450 ml of dry acetone was refluxed with stirring for 24 hrs under argon atmosphere. After cooling, the insoluble material was removed by filtration and the filtrate was evaporated. The residue was diluted with ethyl acetate, washed with water, 1% NaOH and brine, dried over anhydrous sodium sulfate, and evaporated under reduced pressure to give a solid, which was recrystallized from hexane-benzene to give 26.5 g of 4'-(2-(N-benzyloxycarbonylamino)ethoxy)-acetophenone as white needles.

m.p.: 80°–81° C.,

IR (KBr): 3310, 1690, 1666, 1600, 1560, 1356, 1273, 1257, 1165, 1112, 1055, 837, 826, 750, 698 cm$^{-1}$.

MS (EI, 20eV): m/z 313 (M+),

NMR(CDCl$_3$): δ=2.55(3H,s), 3.63(2H,dt,J=5.0, 5.3Hz), 4.10(2H,t,J=5.0Hz), 5.11(2H,s), 5.27(1H,br.t), 6.90(2H,d,J=8.7Hz), 7.27–7.42(5H,m), 7.92(2H,d,J=8.7Hz), (4) A mixture of 21 g of the resulting product, 7.44 g of selenium dioxide, 1.35 ml of water and 34 ml of dioxane was refluxed for 20 hrs. After removal of selenium, the solvent was evaporated to give a viscous oil, which was treated with 300 ml of water at 100° C. for 3 hrs with stirring. The solution was concentrated to give 23 g of 4-(2-(N-benzyloxycarbonylamino)ethoxy)phenylglyoxal hydrate as an oil, which was used in the next reaction without further purification.

(5) To a solution of 4-(2-(N-benzyloxycarbonylamino)-ethoxy)phenylglyoxal hydrate (16 g) in methanol (60 ml) and 1,4-dioxane (60 ml), a solution of 2-aminoacetamidine dihydrobromide (11 g) in water was added at −15° C. A 20% KOH solution (32 ml) was added thereto and the mixture was stirred at −15° C. for 1 hr and at room temperature for 1 hr. The solvent was removed under reduced pressure and the residue was dried to give a crude solid, which was triturated with 2-propanol. The insoluble solid was collected by filtration, washed with cold 2-propanol, and dried to give 5.9 g of 2-amino-5-(4-(2-(N-benzyloxycarbonylamino)ethoxy)phenyl)pyradine as pale yellow crystals.

m.p.: 128°–130° C.

IR (KBr): 3380, 3175, 1686, 1601, 1522, 1504, 1478, 1458, 1259, 1250, 1193, 1140, 1010, 820, 696 cm$^{-1}$.

MS (EI, 20eV): m/z 364 (M+),

NMR(CDCl$_3$): δ=3.63(2H,dt,J=5.0, 5.2Hz), 4.08(2H,t,J=5.0Hz), 4.61(2H,br.s), 5.13(2H,s), 5.35(1H,br.t), 6.94(2H,d,J=8.7Hz), 7.26–7.42(5H,m), 7.78(2H,d,J=8.7Hz), 8.02(1H,d,J=1.4Hz), 8.36(1H,d,J=1.4Hz), (6) The resulting product (1.0 g) and methylglyoxal (5.55 mmol) were dissolved in 23 ml of methanol, and 0.55 ml of conc hydrochloric acid was added thereto at room temperature under argon atmosphere. The mixture was stirred at 70° C. for 4 hrs and condensed to a crude powder, which was triturated with water. The precipitated solid was filtered, washed with water and ether, and dried to give 1.2 g of 6-(4-(2-(N-benzyloxycarbonylamino)ethoxy)phenyl)-3,7-dihydro-2-methylimidazo[1,2-a]pyradin-3-one hydrochloride as yellow crystals.

m.p.: 152°–155° C.

IR (KBr): 3350, 3100–2000, 1700, 1652, 1598, 1500, 1241, 830 cm$^{-1}$.

MS (SIMS): m/z 419 (M+H). NMR(CDCl$_3$): δ=2.56(3H,s), 3.54(2H,t,J=5.6Hz), 4.11(2H,t,J=5.6Hz), 5.09(2H,s), 7.08(2H,d,J=8.6Hz), 7.22–7.40(5H,m), 7.89(2H,d,J=8.6Hz), 8.53(1H,d,J=1.1Hz), 9.04(1H,d,J=1.1Hz), (7) A mixture of the resulting product (500 mg) and anhydrous hydrogen bromide in acetic acid (30% solution, 1.2 ml) was stirred at room temperature for 10 minutes. Ether was added to the mixture and the precipitated solid was filtered, washed with ether, followed by chloroform, and dried to give 490 mg of 6-(4-(2-aminoethoxy)phenyl)-3,7-dihydro-2-methylimidazo[1,2- a]pyradin-3-one dihydrobromide as a hygroscopic powder.

MS (SIMS): m/z 285 (M+H).

NMR(CD$_3$OD): δ=2 58(3H,s), 3.44(2H,t,J=4.9Hz), 4.36(2H,t,J=4.9Hz), 7.21(2H,d,J=8.7Hz), 8.01(2H,d,J=8.7Hz), 8.65(1H,br.s), 9.16(1H,br.s).

(8) The resulting product (525 mg) was dissolved in 10 ml of water, and a 5% solution of sodium hydrogencarbonate was added thereto until the pH 9. 460 mg of fluorescein isothiocyanate in acetone was added, and the mixture was stirred for 2 hrs. The reaction was stopped by acidifying with acetic acid to pH 4.5, and the precipitated solid was collected by filtration, washed with water, acetone, methanol followed by ether to give 450 mg of 3,7-dihydro-6-(4-(2-(N'-(5-fluoresceinyl)thioureido)ethoxy)phenyl)-2-methylimidazo[1,2-a]pyradine-3-one (Compound 1) as yellow crystals.

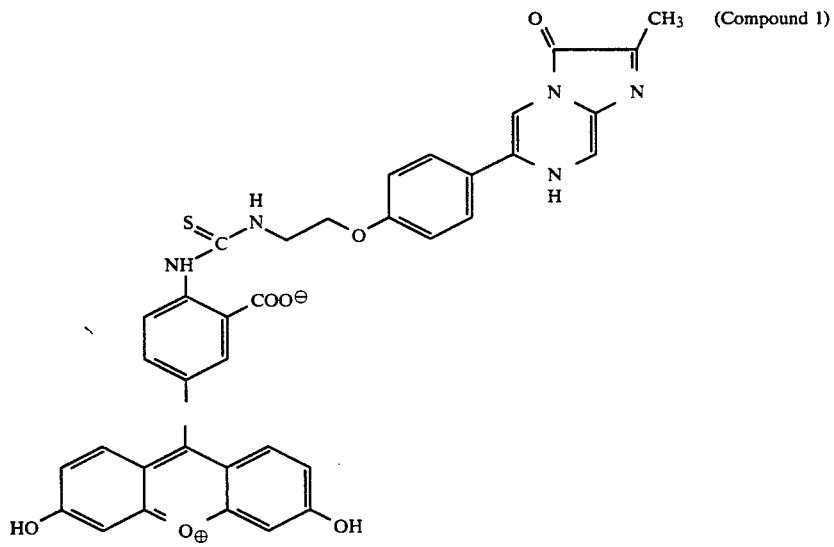

(Compound 1)

m.p.: 226°-228° C. (decomposition).

IR (KBr): 3700-2000, 1602, 1580, 1505, 1461, 1245, 1175, 1106, 835 cm$^{-1}$.

MS (SIMS): m/z 674 (M+H).

UV: λ$_{max}$=284, 355, 452 nm (in MeOH), λ$_{max}$=253, 265, 440 nm (in MeOH-HCl), λ$_{max}$=240, 265, 495 nm (in MeOH-NaOH).

NMR(CDCl$_3$/CD$_3$OD=1/1): δ=2.50(3H,s,m), 4.14(2H,t,J=5.6Hz), 4.32(2H,t,J=5.6Hz), 6.55(2H,dd,J=2.4, 8.6Hz), 6.70(2H,d,J=2.5Hz), 6.72(2H,d,J=8.6Hz), 7.10(2H,d,J=10.9Hz), 7.15(1H,d,J=8.3Hz), 7.58(2H,d,J=10.9Hz), 7.59(1H,br.s), 7.73(1H,br.s), 7.87(1H,dd,J=2.1, 8.3Hz), 8.11(1H,d,J=2.1Hz).

EXAMPLE 2

Compound 1 (1.8 g) was snspended in methanol, and 225 mg of sodium hydrogencarbonate in water (90 ml) was added thereto at room temperature. After stirring at room temperature for 30 minutes, the solution was warmed until becoming transparent and condensed under reduced pressure. To the residue, 20 ml of methanol and 100 ml of ether were added. The precipitated solid was collected by filtration, washed with ether, and dried to give 1.71 g of sodium salt of Compound 1 m.p. 228°-232 ° C. (decomposition).

IR (KBr): 3700-2000, 1630, 1582, 1510, 1470, 1382, 1320, 1250, 1210, 1108, 850 cm$^{-1}$.

MS (SIMS): m/z 674 (M+H), 697(M+Na+1), 719(M+2Na).

UV: λ$_{max}$=455, 485 nm (in water), λ$_{max}$=492 nm (in water-HCl), λ$_{max}$=443 nm (in water-NaOH).

NMR(CDCl$_3$/CD$_3$OD=1/1): δ=2.50(3H,s), 4.13(2H,t,J=5.2Hz), 4.13(2H,t,J=5.2Hz), 4.33(2H,t,J=5.2Hz), 6.78(2H,dd,J=2.2, 8.9Hz), 6.93(2H,d,J=2.2Hz), 7.01(2H,d,J=8.9Hz), 7.12(2H,d,J=8.8Hz), 7.20(1H,d,J=8.3Hz), 7.63(2H,d,J=8.8Hz), 7.70(1H,br.s), 7.92(1H,br.s), 8.00(1H,dd,J=2.0, 8.3Hz), 8.34(1H,d,J=2.0Hz).

Measurement of Chemiluminescence Spectrum 3 ml of 0.01M cetyltrimethylammonium bromide in 0.1M phosphate buffer (pH 7.0) was put into a quart glass cell. About 10 μg of Compound 1 of the present invention was added thereto and dissolved, and then chemiluminescence spectrum was immediately measured with a luminescence spectrometer. The result is shown in FIG. 1.

As shown by the result of the measurement of chemiluminescence spectrum in FIG. 1, maximum fluorescence emitted by Compound 1 was measured at 532 nm in chemiluminescence system. In comparison to the luminescence wavelengths (380 nm) of 2-methyl-6-phenyl-3,7-dihydroimidazo[1,2-a]pyradin-3-one which is often used as a chemiluminescence reagent, Compound 1 of the present invention has 150 nm longer luminescence wavelengths. Therefore, it is advantageously possible to measure the emitted chemiluminescence by using the compounds of the present invention with little interference of the living body's components having absorption or fluorescence in the visible region.

The luciferin derivatives of the present invention, which are prepared by a covalent combination of a fluorescence probe with a luciferin compound, are novel compounds making it possible to detect active oxygen by the characteristic luminescence in long wavelengths region. Compared with the conventional chemiluminescence substances, the compounds of this invention can emit a longer wavelengths luminescence, so that the compounds of the present invention are very useful as chemiluminescence reagents for emission spectrochemical analyses, for example, the determination of active oxygen in living body's samples containing many interfering substances, or the analyses of various living body's component substances in combination with a in vivo system producing active oxygen and/or an enzymatic system relating to production of active oxygen.

What is claimed is:

1. A compound of the formula

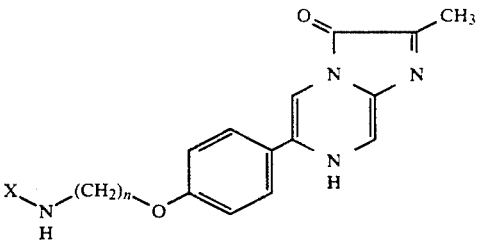

wherein X is hydrogen, benzyloxycarbonyl, p-methoxybenxyloxycarbonyl, p-chlorobenzyloxycarbonyl, p-nitrobenzyloxycarbonyl, p-phenylazobenzyloxycarbonyl, p-methoxyphenylazobenzyloxycarbonyl, t-butoxycarbonyl, t-methoxyphenylazobenzyloxycarbonyl, t-butoxycarbonyl, t-amyloxycarbonyl, p-biphenylisopropyloxycarbonyl, diisopropylmethyloxycarbonyl, formyl, R—, R—CO—, R—$SO_2$—, R—NHCO— or R—NHCS—; R is a fluoroesence probe having an excited wavelength range of from 400 nm to 530 nm; and n represents an integer of 1 to 4; or a salt thereof.

2. A compound according to claim 1, wherein X is R—, R—CO—, R—$SO_2$—, R—NHCO— or R—NHCS—.

3. A compound according to claim 2, wherein X is R—NHCS—.

4. A compound according to claim 2, wherein R is fluorescein.

* * * * *